(12) United States Patent
Morns et al.

(10) Patent No.: US 7,747,049 B2
(45) Date of Patent: Jun. 29, 2010

(54) METHOD OF ANALYSING A REPRESENTATION OF A SEPARATION PATTERN

(75) Inventors: Ian Morns, Tyne & Wear (GB); Anna Kapferer, Newcastle upon Tyne (GB); David Bramwell, Newcastle Upon Tyne (GB)

(73) Assignee: BioSignatures Limited (GB)

( * ) Notice: Subject to any disclaimer, the term of this patent is extended or adjusted under 35 U.S.C. 154(b) by 1244 days.

(21) Appl. No.: 11/212,478

(22) Filed: Aug. 26, 2005

(65) Prior Publication Data

US 2007/0014450 A1 Jan. 18, 2007

(30) Foreign Application Priority Data

Jul. 15, 2005 (GB) .................................... 0514553

(51) Int. Cl.
G06K 9/00 (2006.01)
G01N 33/48 (2006.01)
G01N 33/50 (2006.01)

(52) U.S. Cl. ........................................ 382/128; 702/19
(58) Field of Classification Search ................. 382/128, 382/129–134; 702/19–21
See application file for complete search history.

(56) References Cited

U.S. PATENT DOCUMENTS

| 4,969,204 | A | | 11/1990 | Jones et al. ................. 382/240 |
| 5,073,963 | A | | 12/1991 | Sammons et al. ........... 382/128 |
| 5,980,096 | A | | 11/1999 | Thalhammer-Reyero |
| 6,064,754 | A | * | 5/2000 | Parekh et al. ................ 382/129 |
| 6,219,462 | B1 | | 4/2001 | Anandan et al. ............. 382/294 |
| 6,277,259 | B1 | * | 8/2001 | Guttman et al. ............. 204/461 |
| 6,294,136 | B1 | | 9/2001 | Schwartz |
| 6,404,905 | B1 | * | 6/2002 | Taylor, Jr. .................... 382/128 |
| 6,480,618 | B1 | * | 11/2002 | Parekh et al. ................ 382/129 |
| 6,513,025 | B1 | | 1/2003 | Rosen .......................... 706/45 |
| 6,597,996 | B1 | | 7/2003 | Venkataraman et al. |
| 6,675,104 | B2 | | 1/2004 | Paulse et al. .................. 702/22 |

(Continued)

FOREIGN PATENT DOCUMENTS

EP 1298505 4/2003

(Continued)

OTHER PUBLICATIONS

Rosengren, et al.; "Comparison of PDQuest and Progenesis software packages in the analysis of two-dimensional electrophoresis gels," Proteomics, vol. 3, No. 10, Oct. 2003 pp. 1936-1946.

(Continued)

*Primary Examiner*—Aaron W Carter
(74) *Attorney, Agent, or Firm*—Clise, Billion & Cyr, P.A.; Tim Clise

(57) ABSTRACT

The invention relates principally to the statistical analysis of protein separation patterns. The invention solves the problems associated with producing models which are predictive of classification using unreduced data. The invention provides a method of analysing a representation of a separation pattern, the representation including a neighborhood representing a region of the separation pattern, the neighborhood including a plurality of data points, the method comprising augmenting data by representing the entire region using each data point of the neighborhood; and building a classification model using some or all of the data points.

29 Claims, 3 Drawing Sheets

U.S. PATENT DOCUMENTS

| | | |
|---|---|---|
| 7,107,254 B1 * | 9/2006 | Dumais et al. ............... 706/50 |
| 7,110,889 B2 | 9/2006 | Venkataraman et al. |
| 7,117,100 B2 | 10/2006 | Venkataraman et al. |
| 7,139,666 B2 | 11/2006 | Venkataraman et al. |
| 7,333,895 B2 * | 2/2008 | Hitt et al. ..................... 702/19 |
| 2003/0224448 A1 | 12/2003 | Harbury et al. |
| 2004/0002118 A1 | 1/2004 | Smilansky ................. 435/7.1 |
| 2004/0002930 A1 | 1/2004 | Oliver et al. ................. 706/46 |
| 2004/0019574 A1 * | 1/2004 | Meng et al. .................. 706/15 |
| 2004/0024532 A1 | 2/2004 | Kincaid ....................... 702/19 |
| 2004/0038417 A1 * | 2/2004 | Cahill et al. ................. 436/86 |
| 2004/0098208 A1 | 5/2004 | Reeve et al. ................. 702/32 |
| 2004/0193378 A1 | 9/2004 | Gut et al. ..................... 702/20 |
| 2005/0018887 A1 | 1/2005 | Breen ......................... 382/128 |
| 2005/0032113 A1 * | 2/2005 | Tanaka et al. ............... 435/7.1 |
| 2005/0060102 A1 | 3/2005 | O'Reilly et al. |
| 2005/0075875 A1 * | 4/2005 | Shozakai et al. ............ 704/231 |
| 2005/0100967 A1 | 5/2005 | Leslie et al. ................ 435/7.1 |
| 2005/0129302 A1 | 6/2005 | Smilansky et al. .......... 382/149 |
| 2005/0129303 A1 | 6/2005 | Smilansky et al. .......... 382/149 |
| 2005/0234656 A1 | 10/2005 | Schwartz et al. |
| 2006/0147924 A1 | 7/2006 | Ramsing et al. |
| 2007/0014450 A1 | 1/2007 | Morns et al. |
| 2007/0016606 A1 | 1/2007 | Morns et al. |
| 2007/0276610 A1 * | 11/2007 | Korenberg .................. 702/19 |
| 2009/0055100 A1 * | 2/2009 | Cahill et al. ................. 702/19 |

FOREIGN PATENT DOCUMENTS

| | | |
|---|---|---|
| EP | 1238366 | 4/2004 |
| GB | 2413695 | 11/2005 |
| GB | 2413696 | 11/2006 |
| WO | WO0145046 | 6/2001 |
| WO | WO03076896 | 9/2003 |
| WO | WO2004050825 | 6/2004 |
| WO | WO2004063990 | 7/2004 |
| WO | WO2005103706 | 11/2005 |

OTHER PUBLICATIONS

M.R. Wilkins, et al (eds.), "Proteome Research: New Frontiers in Functional Genomics", Springer-Verlag, Berlin Heidelberg 1997 (132 pages, representing entire book).

International Search Report from PCT/GB2006/002548 dated Nov. 1, 2006 (5 pages).

International Search Report from PCT/GB2006/002581 dated Oct. 31, 2006 (4 pages).

International Search Report from PCT/GB2006/002585 dated Oct. 13, 2006 (5 pages).

Weinert, et al., "Neural networks for protein classification," Applied Bioinformatics, vol. 3, No. 1, Dec. 7, 2004, 17 pages.

* cited by examiner

METHOD OF ANALYSING A REPRESENTATION OF A SEPARATION PATTERN

CROSS-REFERENCES TO RELATED APPLICATIONS

This application claims the benefit of United Kingdom Application Serial Number 0514553.7, filed Jul. 15, 2005, which application is incorporated herein by reference.

This application is related to, titled: A METHOD OF ANALYSING SEPARATION PATTERNS, U.S. application Ser. No. 11/212,477, and, titled: A METHOD OF ANALYSING REPRESENTATIONS OF SEPARATION PATTERNS, U.S. application Ser. No. 11/212,479, both of which are filed on even date herewith and incorporated by reference

FIELD OF THE INVENTION

The invention relates principally to the statistical analysis of protein separation patterns, and in particular to a method of data augmentation able to reduce the number of variables used in the building of a classification model.

BACKGROUND OF THE INVENTION

A large proportion of supervised learning algorithms suffer from having large numbers of variables in comparison to the number of class examples. With such a high ratio, it is often possible to build a classification model that has perfect discrimination performance, but the properties of the model may be undesirable in that it lacks generality, and that it is far too complex (given the task) and very difficult to examine for important factors.

It is desirable to overcome some or all of the above-described problems.

SUMMARY OF THE INVENTION

According to a first aspect of the invention, there is provided a method of performing an operation on a protein sample for the analysis of a representation of a separation pattern, the representation including a neighborhood representing a region of the separation pattern, the neighborhood including a plurality of data points, the method comprising augmenting data by representing the entire region using each data point of the neighborhood; and building a classification model using some or all of the data points.

By "representation" is meant any image, vector, table, database, or other collection of data representing a separation pattern. The data may have any dimensionality. By "separation pattern" is meant the result of any separation technique, including, but not limited to, gel electrophoresis, mass spectrometry, liquid chromatography, affinity binding, and capillary electrophoresis.

By "data point" is meant any constituent unit of data in the representation.

For example, in one embodiment, the representation is a two-dimensional image of a separation pattern obtained by gel electrophoresis, each pixel of the image constituting a data point.

The invention exploits the fact that data points in a representation of a separation pattern are usually highly locally correlated, i.e. there is usually far more resolution in the representation than in the signal which is represented.

By taking each data point of the neighborhood as being representative of the entire region covered by that neighborhood, the resolution of the representation is effectively reduced, while the number of measurements of that region is effectively increased.

Reducing the resolution of the representation reduces the number of variables used in the building of a classification model. Thus, the model is more likely to offer less than perfect performance, allowing a range of model performances to be obtained and facilitating the identification of parts of the separation pattern which are important in predicting its classification.

Unlike other data reduction processes, for example simple averaging, the invention does not discard data: each data point of a neighborhood is taken as being an independent measurement of the region of the separation pattern covered by that neighborhood, effectively increasing the number of separation patterns used in the model building process.

In addition, sensor-added noise is usually of a relatively high frequency, affecting few successive data points in the representation. The invention mitigates the impact of such noise as several measurements of the region covered by a neighborhood are taken.

Thus, in effect, the invention trades resolution for class examples. This has several advantages:
 an improvement in supervised learning ability
 an improvement in the generality of the classification model
 reduced dimensionality
 improved tolerance to noise.

In one embodiment, the data augmentation step includes separating the data points of the neighborhood into respective recombined representations, the location of a data point in a recombined representation corresponding to the location of its neighborhood in the representation. In this way, an original representation may be transformed into a number of recombined representations each having a lower resolution. When a classification model is built, the recombined representations may be treated as though each represents a different separation pattern.

The method may include associating each recombined representation with a particular location of a data point in a neighborhood. Maintaining this association constant throughout the procedure provides for computational efficiency. Alternatively, the association of recombined representations with locations may be varied between neighborhoods. This is computationally more difficult, but can reveal any effect of a particular association.

The method may include varying the position of a particular neighborhood in relation to the representation. This reveals whether the chosen position of that neighborhood results in artefacts being obtained.

The method may include comparing a first distribution built using neighborhoods of a first size to a second distribution built using neighborhoods of a second size and selecting criteria based on the first and second sizes if a statistical change in the distributions is detected.

F-ratio or student t tests may be used to determine a probability threshold based on the probability that the distributions significantly differ in means. Alternatively, non-parametric tests may be used.

The method may include building a distribution in respect of each data point, the distribution including values of neighbouring data points.

This results in a distribution of likely values for each data point in the representation. The distributions of the neighbours of each data point can be used to predict how likely the value of that data point is, given what the case is in the rest of the representation. If all of the neighbours indicate that the value of the data point is unlikely, that data point probably represents a noise feature. This approach only works if the neighbours are good predictors of each other. As the size of the neighborhood increases, the prediction performance of the neighbours will decrease.

The method may include determining the number of data points the values of which are unlikely given the distributions associated with those data points.

This produces a measure of correlation.

The method may include determining the absolute difference between the actual value of each data point and a value predicted using the distribution associated with that data point.

Again, this provides a measure of local correlation.

According to a second aspect of the invention, there is provided a method of analysing a representation of a separation pattern, the representation including a neighborhood representing a region of the separation pattern, the neighborhood including a plurality of data points, the method comprising augmenting data by representing the entire region using each data point of the neighborhood; and building a classification model using some or all of the data points.

The method of the second aspect of the invention may include any feature of the method of the first aspect of the invention.

According to the first aspect of the invention, there is provided apparatus for performing operations on protein samples for the analysis of a representation of a separation pattern, the representation including a neighborhood representing a region of the separation pattern, the neighborhood including a plurality of data points, the apparatus comprising means for augmenting data by representing the entire region using each data point of the neighborhood; and building a classification model using some or all of the data points.

According to the second aspect of the invention, there is provided apparatus for analysing a representation of a separation pattern, the representation including a neighborhood representing a region of the separation pattern, the neighborhood including a plurality of data points, the apparatus comprising means for augmenting data by representing the entire region using each data point of the neighborhood; and building a classification model using some or all of the data points.

According to the invention, there is also provided a computer program directly loadable into the internal memory of a digital computer, comprising software code portions for performing a method of the invention when said program is run on the digital computer.

According to the invention, there is also provided a computer program product directly loadable into the internal memory of a digital computer, comprising software code portions for performing a method of the invention when said product is run on the digital computer.

According to the invention, there is also provided a carrier, which may comprise electronic signals, for a computer program of the invention.

According to the invention, there is also provided electronic distribution of a computer program or a computer program product or a carrier of the invention.

BRIEF DESCRIPTION OF THE DRAWINGS

In order that the invention may more readily be understood, a description is now given, by way of example only, reference being made to the accompanying drawings, in which.

DETAILED DESCRIPTION OF THE INVENTION

Figure 1:
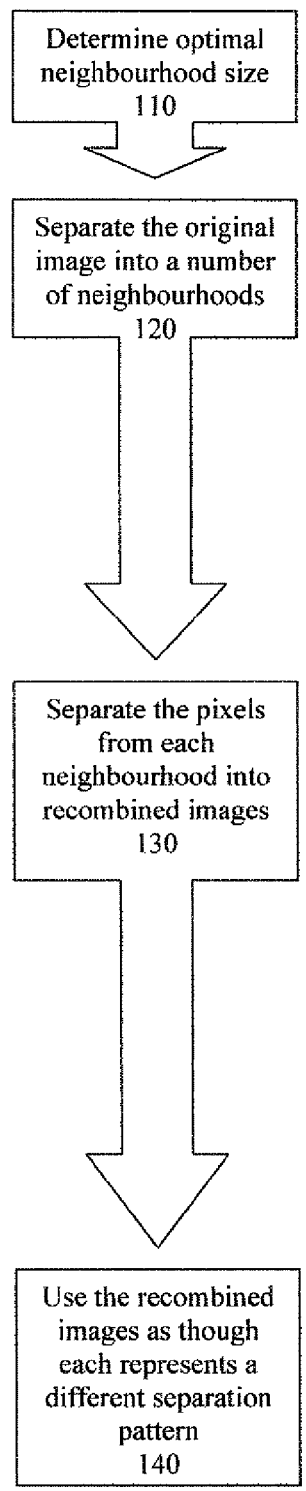
FIG. 1 is a flowchart representing a method of augmenting data according to the invention.
Figure 1:
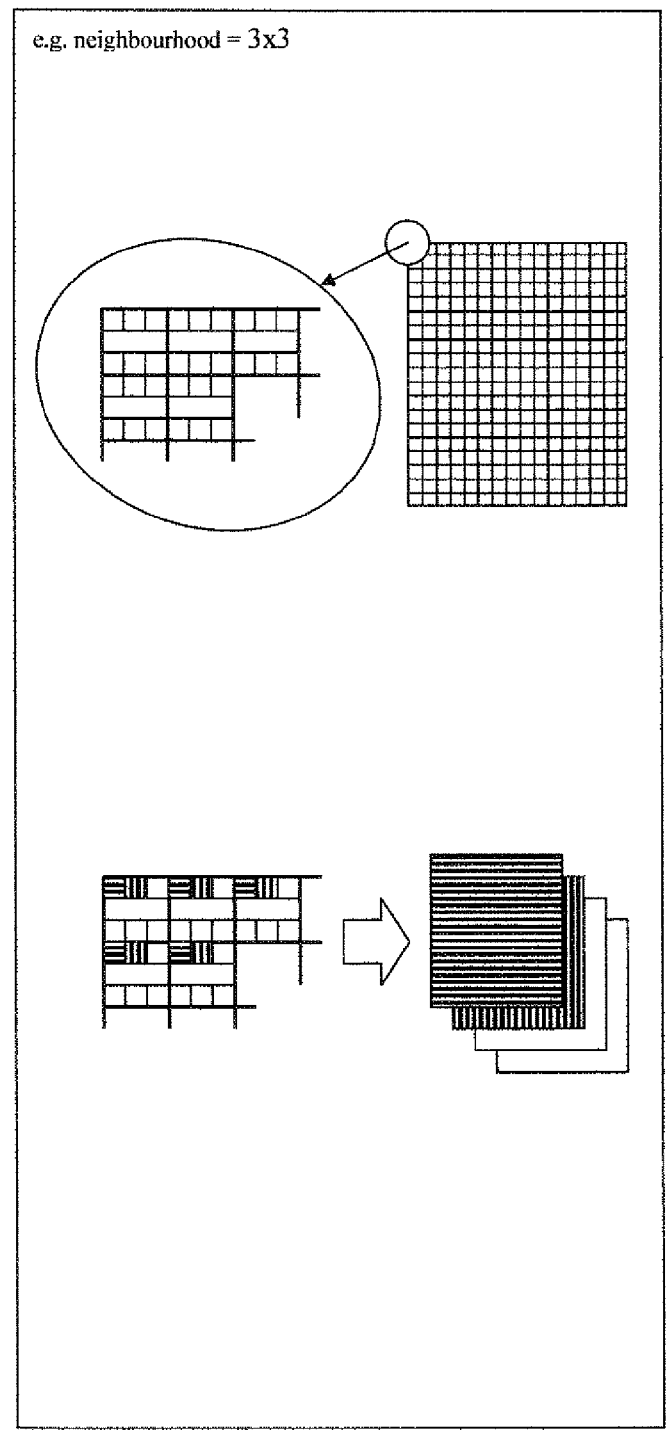

FIG. 1 is a flowchart representing a method of augmenting data according to the invention, the method being applied in relation to a single image. The process is repeated for a number of images representing different separation patterns.

In step 110, the optimal size of a neighborhood is determined. In this embodiment, the size of each neighborhood is 3×3 pixels.

The neighborhood may be of such a size that it covers uncorrelated features. To determine whether or not this is the case, a distribution can be built from a 3×3 neighborhood, for example, and compared to a distribution produced by the extra pixels included in a 5×5 neighborhood. Criteria can be selected based on the neighborhood sizes if a statistical change in the distributions is detected. For example, F-ratio or student t tests provide good tests where a probability threshold can be chosen which allows a threshold based on the probability that the distributions significantly differ in means. Similarly, non-parametric tests could be used.

Alternatively, pixel based statistical prediction models can be built from the whole image to see how well the value of a given pixel can be predicted, given a set of neighborhoods. If the prediction deteriorates then the correlation is dropping. This technique is related to a Bayesian approach. For example, for each pixel of a given value, the neighbouring pixels can be added to a distribution for that given value. This results in a distribution of likely neighborhood values for each pixel in the image. The distributions of the neighbours of each pixel value can be used to predict how likely the value is, given what the case is in the rest of the image. If all of the neighbours indicate that the pixel value is unlikely, that pixel is probably a noise feature. This approach only works if the neighbours are good predictors of each other. As the size of the neighborhood increases, the prediction performance of the neighbours will decrease.

Based on the above approach, a determination of whether the size of the neighborhood is too large can be made in one or both of two ways. Firstly, the number of pixels which are classed as unlikely given their neighbours can be determined. This produces a measure of correlation. Secondly, the neighbours can be used to predict the most likely values of pixels, followed by recording the absolute differences between predicted and actual values. Again, this provides a measure of local correlation.

In step 120, the original image is separated into a number of neighborhoods.

Figure 2:
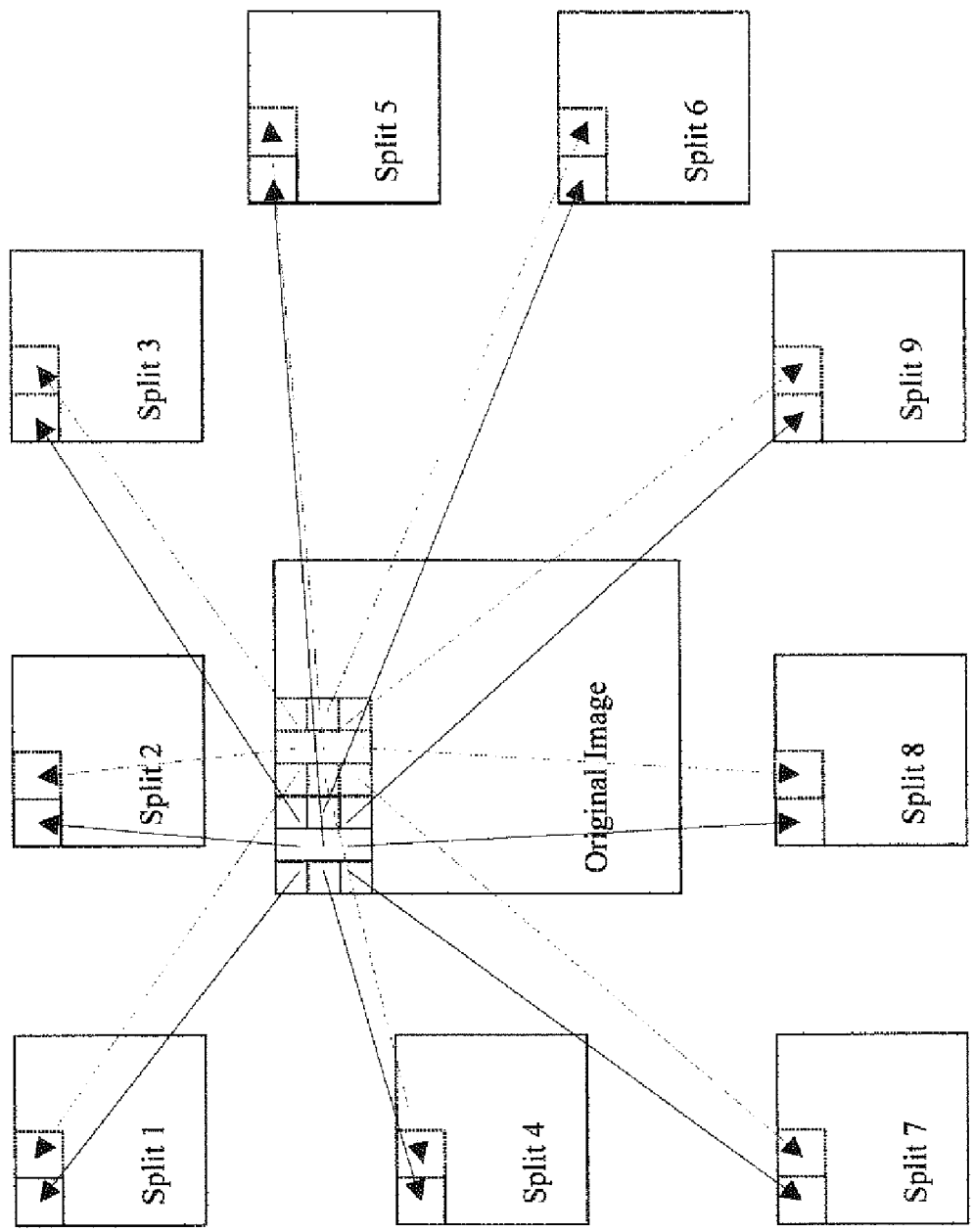
FIG. 2 illustrates one step of the method of FIG. 1 being performed on an image.

FIG. 2 illustrates step 130, in which the pixels from each neighborhood in the original image are separated into recombined images.

The number of recombined images is equal to the number of locations in the neighborhood. For ease of reference, the locations of the pixels in each neighborhood will be referred to as locations 1 to 9, reading from left to right and top to bottom. As seen, a neighborhood of size 3×3 pixels, having nine locations, gives rise to nine recombined images, designated "Split 1" to "Split 9".

Each recombined image is associated with a particular location of a pixel in a neighborhood. For example, a pixel at location 1 in a neighborhood is separated into recombined image "Split 1", a pixel at location 2 is separated into "Split 2", and so on.

The separation of pixels into recombined images is performed for each neighborhood.

The location of a data point in a recombined image corresponds to the location of its neighborhood in the original image.

For example, the neighborhood shown in solid lines in FIG. 2 is in the top left-hand corner of the original image. Therefore, the pixel at location 3 of that neighborhood is separated into the top left-hand corner of recombined image "Split 3". The pixel at location 3 of the neighborhood immediately to the right of the top left-hand neighborhood, shown in dotted lines, will be separated into a location in Split 3 which is immediately to the right of the pixel separated from the neighborhood shown in solid lines, and so on.

For a neighborhood of size 3×3 pixels, each recombined image is one third of the width and height of the original image.

Referring again to FIG. 1, in step 140, the recombined images are used as new class examples. The effect of this is that each pixel in a recombined image is taken as being representative of the region of the separation pattern covered by the neighborhood from which that pixel was taken.

It should be understood that it is not necessary physically to separate pixels into recombined images and to store the recombined images. For example, in a variant, the augmentation is performed during the preparation for each iteration of an importance map building step (described below), by taking pixels directly from unaugmented images.

Figure 3:
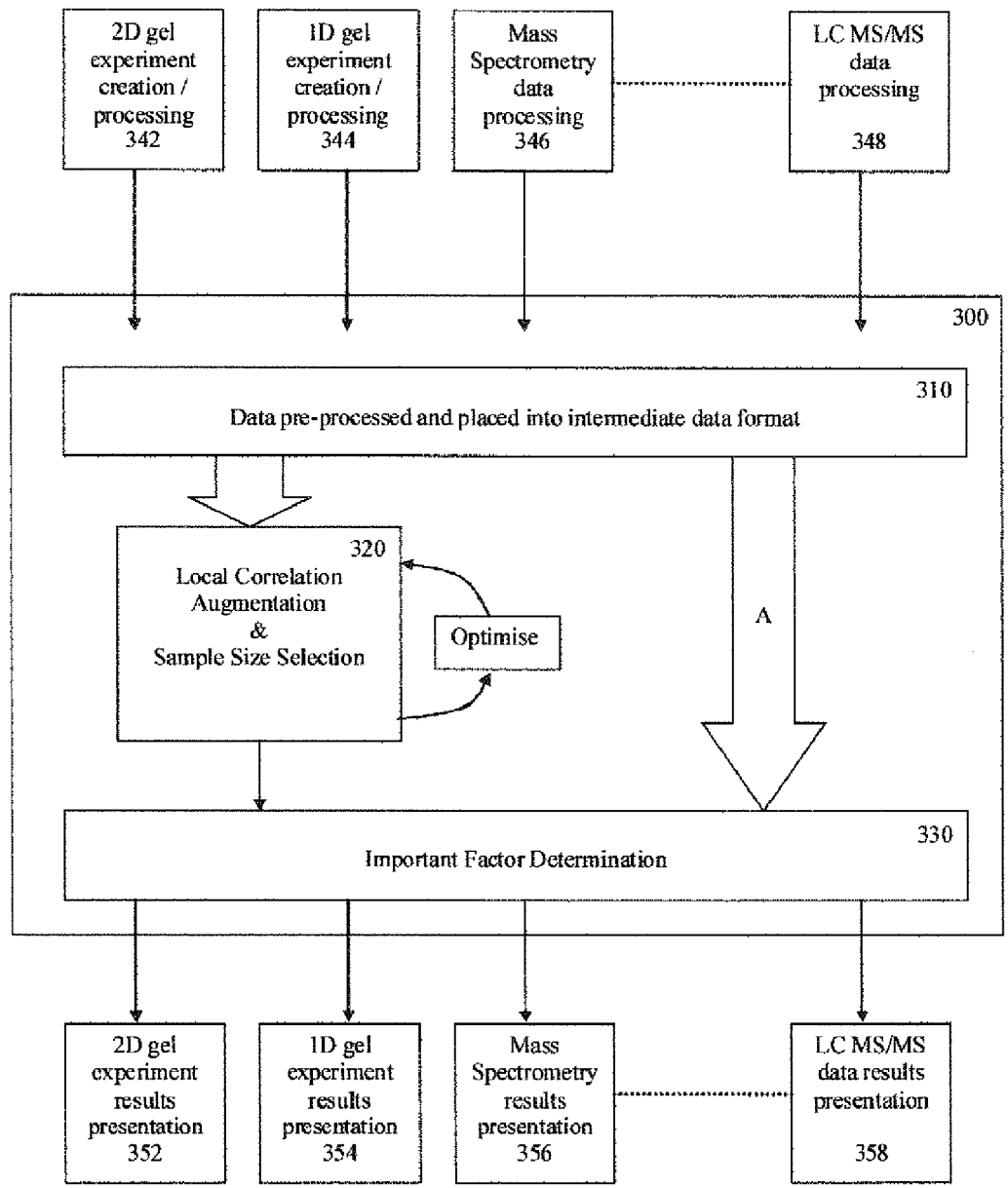
FIG. 3 is a schematic diagram of software according to the invention.

FIG. 3 is a schematic diagram of a software entity 300 according to the invention.

The software entity 300 is a generic automated analysis block that operates on supervised data across modalities, i.e. it is not specific to 2D gels, 1D gels, or mass spectra, for example.

In a preferred embodiment, the software entity is incorporated into multi-application computer software for running on standard PC hardware under Microsoft® Windows®. However, it is to be understood that the invention is platform independent and is not limited to any particular form of computer hardware.

The software entity 300 includes a data preprocessing block 310; a local correlation augmentation and subset size determination block 320, for performing the method of the invention; and an important factor determination block 330.

The software entity 300 receives input data from one of a number of input blocks 340, each input block 340 representing a different separation technique. FIG. 3 shows exemplary input blocks designated 342, 344, 346 and 348.

The input data is in the form of several vectors, each having a class label. Each vector includes a number of 16-bit integer or double precision floating point numbers. The input blocks 340 create a uniform format from the diverse formats of data obtained using the various separation techniques. In addition, there is a secondary metadata file that includes a description of the original data format.

In this embodiment, only one input block is used at a time. In a variant, more than one input block is used simultaneously.

Metadata, including class information, is passed directly from the data preprocessing block 310 to the important factor determination block 330, as indicated by arrow A.

The software entity 300 sends output data to a number of output blocks 350. FIG. 3 shows exemplary output blocks designated 352, 354, 356 and 358. Each output block 350 corresponds to an input block 340.

The output blocks 350 receive results in a generic form and map the results to a more accessible form, for example an image or trace. In block 352, the importance map is mapped back onto one of the images from the set. In block 354, the importance map is mapped back to a gel image; in block 356 to a trace; and in block 358 to a 2D representation of the LC MS data.

The importance map can be used to identify regions of a separation pattern which are important in predicting a classification of the separation pattern. Its construction involves repeatedly building classification models and assessing their performance.

The method of the invention augments the data on which those classification models are built.

When the software entity 300 is commercially exploited, the input blocks 340 and output blocks 350 are tailored to the user's specific requirements, which distinction is transparent to the user.

It is to be understood that, while examples of the invention have been described involving software, the invention is equally suitable for being implemented in hardware, or any combination of hardware and software.

Some portions of the preceding description are presented in terms of algorithms and symbolic representations of operations on data bits within a machine, such as computer memory. These algorithmic descriptions and representations are the ways used by those skilled in the data processing arts to most effectively convey the substance of their work to others skilled in the art. An algorithm includes a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussions, terms such as "processing" or "computing" or "calculating" or "determining" or "displaying" or the like, refer to the action and processes of a computer system, or similar computing device, that manipulates and transforms data represented as physical (e.g., electronic) quantities within the computer system's registers and memories into other data similarly represented as physical quantities within the computer system memories or registers or other such information storage, transmission or display devices.

There is also provided electronic distribution of a computer program of or a computer program product or a carrier of the invention. Electronic distribution includes transmission of the instructions through any electronic means such as global computer networks, such as the world wide web, Internet, etc. Other electronic transmission means includes local area networks, wide area networks. The electronic distribution may further include optical transmission and/or storage. Electronic distribution may further include wireless transmission. It will be recognized that these transmission means are not exhaustive and other devices may be used to transmit the data and instructions described herein.

The invention claimed is:

1. A method of performing operations, in a computing device, on protein samples for the analysis of a representation of a separation pattern, the representation including a neighborhood representing a region of the separation pattern, the neighborhood including a plurality of data points relating to the protein samples, the method comprising using a computer to perform: augmenting data by representing the entire region using each data point of the neighborhood; and building a classification model using some or all of the data points.

2. The method of claim 1 wherein augmenting data includes, in a computing device, separating the data points of the neighborhood into respective recombined representations, the location of a data point in a recombined representation corresponding to the location of its neighborhood in the representation.

3. The method of claim 2, comprising associating, in a computing device, each recombined representation with a particular location of a data point in a neighborhood.

4. The method of claim 3, including varying the association of recombined representations with locations between neighborhoods.

5. The method of claim 4, including varying a position of a particular neighborhood in relation to the representation.

6. The method of claim 1 including comparing, in a computing device, a first distribution built using neighborhoods of a first size to a second distribution built using neighborhoods of a second size and selecting criteria based on the first and second sizes if a statistical change in the distributions is detected.

7. The method of claim 6 wherein F-ratio or student t tests are used to determine a probability threshold based on the probability that the distributions significantly differ in means.

8. The method of claim 6 wherein non-parametric tests are used.

9. The method of claim 1 including building a distribution in respect of each data point, the distribution including values of neighboring data points.

10. The method of claim 9 including determining, in a computing device, a number of data points the values of which are unlikely given the distributions associated with those data points.

11. The method of claim 9 including determining, in a computing device, an absolute difference between the actual value of each data point and a value predicted using the distribution associated with that data point.

12. A method of analyzing, in a computing device, a representation of a separation pattern, the representation including a neighborhood representing a region of the separation pattern, the neighborhood including a plurality of data points, the method comprising using a computer to perform: augmenting data by representing the entire region using each data point of the neighborhood; and building a classification model using some or all of the data points.

13. The method of claim 12 wherein augmenting data includes separating, in a computing device, the data points of the neighborhood into respective recombined representations, the location of a data point in a recombined representation corresponding to the location of its neighborhood in the representation.

14. The method of claim 13, comprising associating each recombined representation with a particular location of a data point in a neighborhood.

15. The method of claim 14, including varying the association of recombined representations with locations between neighborhoods.

16. The method of claim 13, including varying the position of a particular neighborhood in relation to the representation.

17. The method of claim 12 including comparing, in a computing device, a first distribution built using neighborhoods of a first size to a second distribution built using neighborhoods of a second size and selecting criteria based on the first and second sizes if a statistical change in the distributions is detected.

18. The method of claim 17, wherein F-ratio or student t tests are used to determine a probability threshold based on the probability that the distributions significantly differ in means.

19. The method of claim 12 wherein non-parametric tests are used.

20. The method of claim 12 including building, in a computing device, a distribution in respect of each data point, the distribution including values of neighboring data points.

21. The method of claim 20 including determining, in a computing device, a number of data points the values of which are unlikely given the distributions associated with those data points.

22. The method of claim 21 including determining, in a computing device, an absolute difference between the actual value of each data point and a value predicted using the distribution associated with that data point.

23. Apparatus for performing operations on protein samples for the analysis of a representation of a separation pattern, the representation including a neighborhood representing a region of the separation pattern, the neighborhood including a plurality of data points, the apparatus comprising means for augmenting data by representing the entire region using each data point of the neighborhood; and building a classification model using some or all of the data points.

24. Apparatus for analyzing a representation of a separation pattern, the representation including a neighborhood representing a region of the separation pattern, the neighborhood including a plurality of data points, the apparatus comprising means for augmenting data by representing the entire region using each data point of the neighborhood; and building a classification model using some or all of the data points.

25. A non-transitory computer-readable medium having computer executable instructions for performing a method of performing operations on protein samples for the analysis of a representation of a separation pattern, the representation including a neighborhood representing a region of the separation pattern, the neighborhood including a plurality of data points, the method comprising augmenting data by representing the entire region using each data point of the neighborhood; and building a classification model using some or all of the data points.

26. The computer-readable medium of claim 25, wherein augmenting data includes separating the data points of the neighborhood into respective recombined representations, the location of a data point in a recombined representation corresponding to the location of its neighborhood in the representation.

27. The computer-readable medium of claim 26, comprising a computer executable instruction to associate each recombined representation with a particular location of a data point in a neighborhood.

28. The computer-readable medium of claim 27, comprising a computer executable instruction to vary at least one of a group consisting of the association of recombined representations with locations between neighborhoods and the position of a particular neighborhood in relation to the representation.

29. The computer-readable medium of claim 25 comprising a computer executable instructions to compare, in a computing device, a first distribution built using neighborhoods of a first size to a second distribution built using neighborhoods of a second size and to select criteria based on the first and second sizes if a statistical change in the distributions is detected.

* * * * *